(12) United States Patent
Deppisch et al.

(10) Patent No.: US 8,454,564 B2
(45) Date of Patent: Jun. 4, 2013

(54) APPLICATOR AND METHOD FOR APPLYING LOCK SOLUTION IN A CATHETER

(75) Inventors: Reinhold Deppisch, Hechingen (DE); Werner Beck, Rottenburg (DE); Ruth Dietrich, Hechingen (DE); Björn Frederik Seidler, Scheessel (DE); Andrea Schnell, Bisingen-Thanheim (DE); Claudia Hildwein, Tübingen (DE)

(73) Assignee: Gambro Lundia AB, Lund (SE)

( * ) Notice: Subject to any disclaimer, the term of this patent is extended or adjusted under 35 U.S.C. 154(b) by 1217 days.

(21) Appl. No.: 11/629,783

(22) PCT Filed: Jun. 15, 2005

(86) PCT No.: PCT/SE2005/000913
§ 371 (c)(1), (2), (4) Date: Feb. 1, 2008

(87) PCT Pub. No.: WO2005/123164
PCT Pub. Date: Dec. 29, 2005

(65) Prior Publication Data
US 2011/0160664 A1    Jun. 30, 2011

Related U.S. Application Data

(60) Provisional application No. 60/580,485, filed on Jun. 17, 2004.

(30) Foreign Application Priority Data

Jun. 17, 2004 (SE) ........................................ 0401569

(51) Int. Cl.
*A61M 5/00* (2006.01)
*A61M 1/00* (2006.01)

(52) U.S. Cl.
USPC ............................ 604/191; 604/110; 604/125

(58) Field of Classification Search
USPC ................. 604/110, 122, 124, 125, 181, 187, 604/191, 192, 199, 200, 218
See application file for complete search history.

(56) References Cited

U.S. PATENT DOCUMENTS

| | | | | |
|---|---|---|---|---|
| 4,027,669 A | * | 6/1977 | Johnston et al. | 604/110 |
| 4,792,329 A | * | 12/1988 | Schreuder | 604/90 |
| 4,929,230 A | * | 5/1990 | Pfleger | 604/90 |
| 5,338,303 A | * | 8/1994 | King et al. | 604/110 |
| 5,755,696 A | * | 5/1998 | Caizza | 604/164.11 |
| 5,788,670 A | * | 8/1998 | Reinhard et al. | 604/89 |
| 6,010,486 A | * | 1/2000 | Carter et al. | 604/195 |

(Continued)

*Primary Examiner* — Victoria P Shumate
(74) *Attorney, Agent, or Firm* — Finnegan, Henderson, Farabow, Garrett & Dunner LLP (57) ABSTRACT

A device for applying a lock solution in a catheter or other access system comprises a syringe (302) having an expulsion arrangement (305, 311) for expelling the lock solution from the device, said expulsion arrangement including a plunger (305) arranged in a housing (304), further comprising a sterile connector (303) for connecting the syringe (302) to the catheter. The connector (303) is arranged to engage a tip (307) of the expulsion arrangement (305, 311) tightly when the syringe (302) is inserted in the connector (303). The connector (303) is arranged to prevent the tip (307) of the expulsion arrangement (305, 311) from entering the catheter. The tip (307) is frangible. A method of applying a lock solution in a catheter or other access system is also disclosed.

20 Claims, 12 Drawing Sheets

U.S. PATENT DOCUMENTS

| | | | |
|---|---|---|---|
| 6,221,052 B1 * | 4/2001 | Caizza et al. | 604/195 |
| 6,517,516 B1 * | 2/2003 | Caizza | 604/110 |
| 6,544,233 B1 * | 4/2003 | Fukui et al. | 604/191 |
| 6,599,269 B1 * | 7/2003 | Lewandowski et al. | 604/110 |
| 6,911,018 B2 * | 6/2005 | Gordon | 604/110 |
| 6,997,910 B2 * | 2/2006 | Howlett et al. | 604/191 |
| 2001/0037091 A1 * | 11/2001 | Wironen et al. | 604/236 |
| 2001/0053886 A1 * | 12/2001 | Caizza | 604/110 |
| 2002/0173753 A1 * | 11/2002 | Caizza et al. | 604/241 |
| 2004/0097875 A1 * | 5/2004 | Bae | 604/89 |
| 2004/0225258 A1 * | 11/2004 | Balestracci | 604/111 |
| 2005/0251096 A1 * | 11/2005 | Armstrong et al. | 604/218 |
| 2006/0189943 A1 * | 8/2006 | Kato et al. | 604/191 |

* cited by examiner

APPLICATOR AND METHOD FOR APPLYING LOCK SOLUTION IN A CATHETER

CROSS REFERENCE TO RELATED APPLICATIONS

This application is a national phase application based on PCT/SE2005/000913, filed Jun. 15, 2005, the content of which is incorporated herein by reference, and claims the priority of Swedish Patent Application No. 0401569-9, filed Jun. 17, 2004, and the benefit of U.S. Provisional Application No. 60/580,485, filed Jun. 17, 2004, the content of both of which is also incorporated herein by reference.

TECHNICAL FIELD OF THE INVENTION

The present invention relates to a device for applying a lock solution in a catheter or other system for access to an organism, a vascular system, tissue structures or hollow organs, said applicator device comprising a syringe having an expulsion arrangement for expelling the lock solution from the device, said expulsion arrangement including a plunger arranged in a housing, further comprising a sterile connector for connecting the syringe to the catheter or other system for access, the connector being arranged to engage a tip of the expulsion arrangement tightly when the expulsion arrangement of the syringe is inserted in the connector.

The invention also relates to a method for applying a lock solution in a catheter or access system.

BACKGROUND ART

When deciding to treat a patient with the help of a catheter, the benefit of the treatment always has to be balanced against the risk of nosocomial infections, since there is always a risk that bacteria or other microorganisms spread by touch or air contamination grow in the catheter. In order to reduce the risk of infections, a lock solution is applied in the catheter when it has been disconnected from e.g. a dialysis machine or due to therapeutic interventions such as application of contrast media or instillation of fluids or medication. The lock solution provides a kind of liquid barrier for growth of bacteria and other microorganisms. It may contain e.g. heparin, citrate or taurolidine.

In order to further reduce the risk of infections and to simplify the application of the'lock solution, pre-filled syringes with lock solution may be used.

Pre-filled syringes are known containing saline solution for rinsing or e.g. a heparin solution for use as lock solution. Such syringes are marketed e.g. by BD under the name BD Posi-Flush™. These syringes are provided with a so-called luer lock for connecting the syringe to the catheter. Although the solutions in the pre-filled syringe are sterile a problem with maintaining sterility remains, since microorganisms may be introduced by touch or air contamination at the opening of the catheter when connecting and disconnecting the syringe.

SUMMARY OF THE INVENTION

The object of the present invention is to alleviate the problems described above.

A specific object of the invention is to provide a pre-filled applicator device for applying lock solution in a catheter or access system, which ensures enhanced operative simplicity during aseptic handling and which reduces the risk of microbial, particle or air contamination.

Another object of the invention is to provide a pre-filled applicator which makes possible a simple procedure for rinsing and locking a catheter or access system.

Yet another object is to provide a method of applying a lock solution which ensures a significant improvement of the aseptic connection procedure with maintained sterility in the catheter or access system.

An object of the invention is also to provide method that simplifies the procedure of rinsing the catheter or access system prior to application of the lock solution.

The device of the invention has a connector which is arranged to prevent the tip of the expulsion arrangement from entering the catheter lumen, the tip being frangible. With such a device, the tip of the expulsion arrangement may be left behind as a stopper in the connector when the device is removed after injecting the lock solution, thus ensuring maintained sterility.

The connector is preferably a luer lock connector. This type of connector ensures a tight connection and may be fitted on most catheters. However, the connector may of course be of any other equivalent design preventing touch contamination during connection to the catheter.

The frangible tip of the expulsion arrangement may, be provided with a peripheral row of indentations. The indentations provide a stress raiser which makes it easy to break off the tip of the expulsion arrangement.

In order to enhance the engagement of the frangible tip of the expulsion arrangement inside the connector, the frangible tip is preferably provided with a substantially radial projection and an inside of the connector provided with a notch, the projection being arranged to engage the notch.

Another way of enhancing the engagement of the tip of the expulsion arrangement inside the connector is to provide the tip of the expulsion arrangement with a conical shape which tightly fits in an inner conical shape of the connector.

In one embodiment, the housing defines a single compartment which contains the solution to be injected. The one-compartment housing allows a particularly simple construction.

In another embodiment, the housing is divided into a first and second compartment. Thus, two different solutions may be injected using the same applicator device.

The first compartment in a tip end of the housing is preferably filled with flushing solution and the second compartment in a back end of the housing is preferably filled with a lock solution. The applicator device of this embodiment may be used for rinsing a catheter and subsequently applying the lock solution. The flushing solution may be e.g. a saline solution.

The expulsion arrangement may further comprise a divider separating the first and second compartments. This is a way of expelling solution first from the first compartment and then from the second compartment.

According to one embodiment of the invention, the divider is a frangible membrane, and a mandrel at the tip end of the housing is arranged to rupture the membrane. In this manner, the two different solutions may be kept separate during storage and the mandrel ruptures the membrane when the plunger, is pressed down to allow solution from the second compartment to pass through the ruptured membrane, into the catheter.

The frangible tip may be arranged on the plunger or on the divider. A suitable placement of the tip may thus be chosen as desired.

As an alternative to a frangible membrane, the device of the invention may comprise a by-pass arranged to shunt the lock solution past the membrane. Thus, lock solution may effectively be injected once the flushing solution has been injected.

In one embodiment of the invention, the divider is a seal including a valve which is openable on pressing down the plunger. This is another way of allowing solution to be expelled from the second compartment into the catheter.

According to an embodiment of the invention, the plunger my be provided with an abutment means for indicating when the first compartment has been emptied. The nurse or physician thus knows when all flushing solution has been inserted, should he/she wish to wait before also injecting the lock solution.

The inventive applicator may provided with an air removal system for removing air bubbles.

The air removal system preferably comprises a chamber separated from the atmosphere by an air permeable membrane and arranged to communicate with the catheter when the syringe is connected to the catheter. In this manner, atmospheric pressure may be established in the chamber and blood with air bubbles will flow out into the chamber.

The method of the invention comprises the steps of:

connecting a sterile connector attached to a tip end of a syringe to the catheter or other access system, injecting the lock solution in the catheter by pressing an expulsion arrangement of the syringe including a plunger, thereby engaging a frangible tip of the expulsion arrangement in the connector, removing the syringe from the connector, leaving behind the frangible tip of the expulsion arrangement which is broken off when removing the syringe, closing a lid on the connector.

By using this method lock solution may easily be applied while ensuring maintained sterility in the catheter.

According to a specific variant of the inventive method flushing solution is injected prior to injecting the lock solution. The catheter or any other access system may thus conveniently be rinsed before application of the lock solution.

In one variant of the method of the invention flushing solution is injected by a first press on the plunger and the lock solution is injected by a second press on the plunger. This is convenient should the nurse or physician wish to wait between rinsing and application of lock solution. An abutment means arranged on the plunger may indicate to the nurse or physician when the flushing solution has been expelled from the syringe.

In another variant the flushing solution and subsequently the lock solution are injected in one continuous press on the plunger. This is a quick way of rinsing the catheter and applying the lock solution.

BRIEF DESCRIPTION OF THE DRAWINGS

The invention will be described in more detail with reference to the appended drawings, which show examples of presently preferred embodiments of the invention.

DETAILED DESCRIPTION OF PREFERRED EMBODIMENTS OF THE INVENTION

Figure 1:
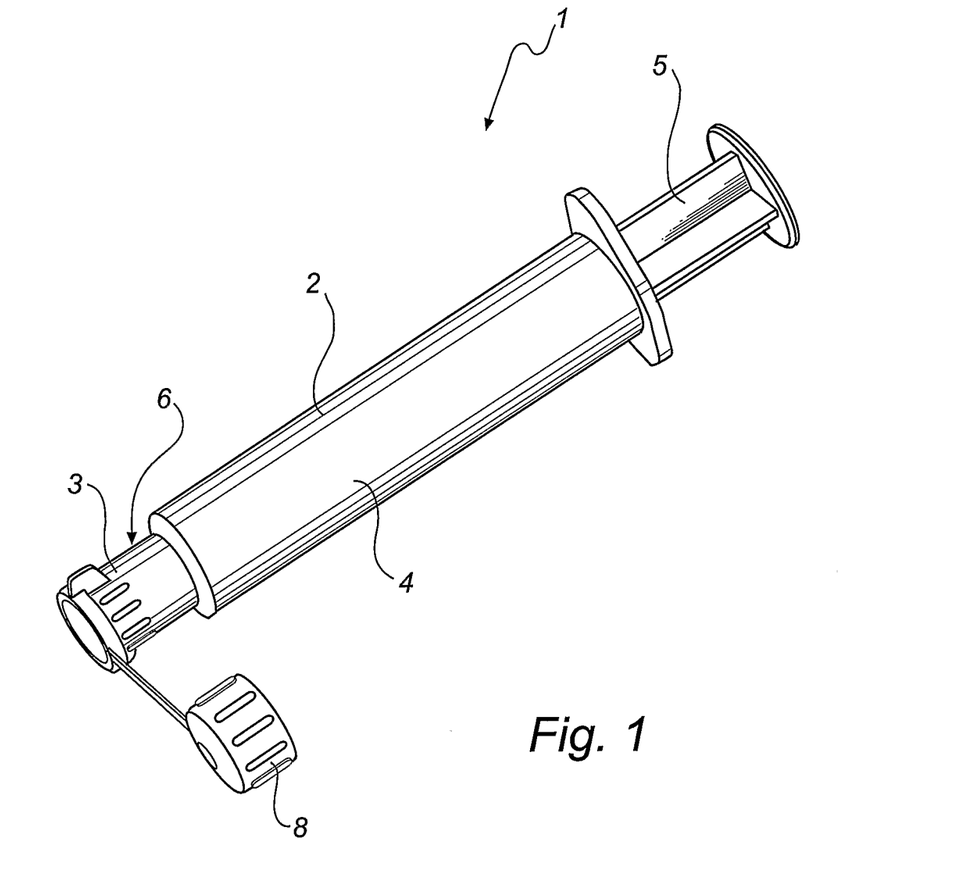
FIG. 1 is a perspective view of an applicator device according to a first embodiment of the invention with one compartment.

The applicator device 1 of FIG. 1 basically consists of a hollow body similar to a syringe 2 provided with a connector in the form of a connector 3 for connection with a catheter or other access system (not shown). The syringe 2 has an elongate housing 4 in which a plunger 5 is coaxially arranged. The plunger 5 constitutes an expulsion arrangement for expelling solution from the syringe. On a tip end 6 of the housing 4 the connector 3 is connected. The plunger 5 has a tip 7 which is frangible.

Figures 2, 3:
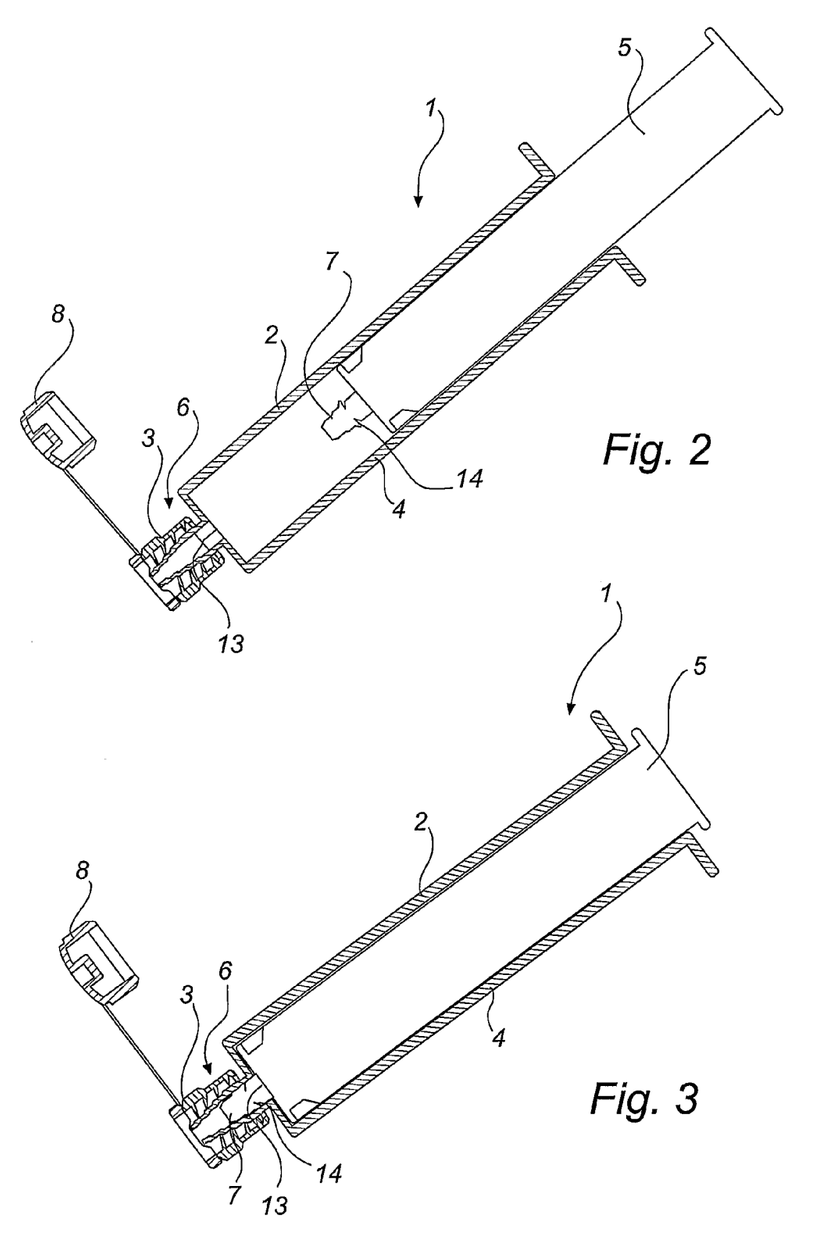
FIG. 2 is a cross-sectional view of the applicator device of FIG. 1 shown before the plunger is pressed.
FIG. 3 is a view corresponding to FIG. 2, but shown when the plunger has been pressed all the way down.

When the catheter has been disconnected from e.g. a dialysis machine or other bloodline system, it is important to make sure that no blood clots are formed in the catheter and that microorganisms are prevented from entering the catheter. Therefore, the catheter is rinsed by means of a separate syringe filled with flushing solution, e.g. saline solution. Once the catheter has been rinsed, a lock solution containing e.g. heparin or taurolidine or any other composition of biologically and physiologically suitable substances may be applied in the lumen of the catheter by means of the applicator device 1. The connector 3 is connected to the catheter and the tip end 6 of the housing 4 is fixed inside the connector 3. When the plunger 5 is pressed down, the lock solution enters the catheter. As the plunger 5 is pressed all the way down the tip 7 is stuck inside the connector 3. The inner shape of the connector 3 and the outer shape of the tip 7 ensure that the tip 7 does not enter the catheter. This may be achieved e.g. by means of projections on the outside of the tip 7 and corresponding notches on the inside of the connector 3 or preferably by the tip being shaped as a cone fitting in an inner cone shape of the connector 3. The tip 7 is provided with a stress raiser in the form of a peripheral row of punctures or indentations 14. Once the tip 7 is stuck inside the connector 3, the syringe 2 may be withdrawn and the broken-off tip 7 left in the connector 3, closing the opening of the connector 3. The tip end 6 of the housing 4 is also broken off and left together with the connector 3. When the syringe 2 has been removed, a lid 8 is placed over the connector 3, which remains connected to the catheter. In this manner, a lock solution is applied in the catheter while maintaining the sterility of the opening of the catheter.

Figure 4:
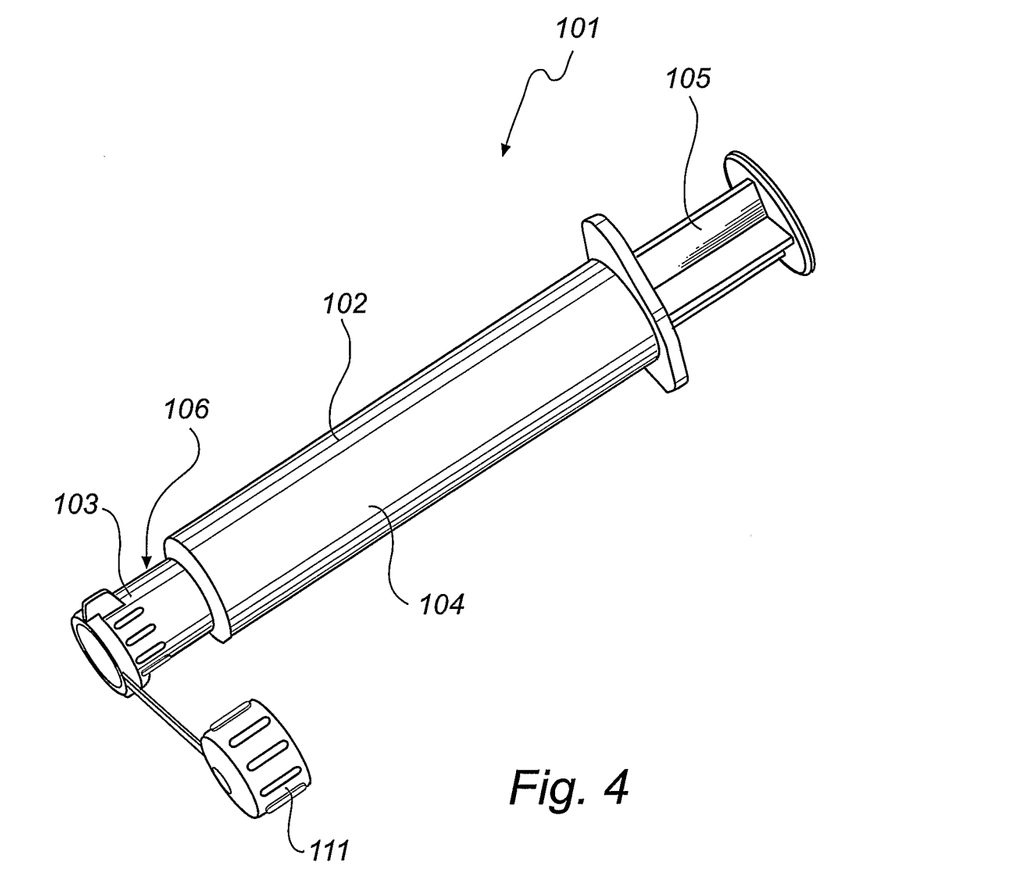
FIG. 4 is a perspective view of an applicator device according to a second embodiment of the invention with two compartments.
Figures 5, 6:
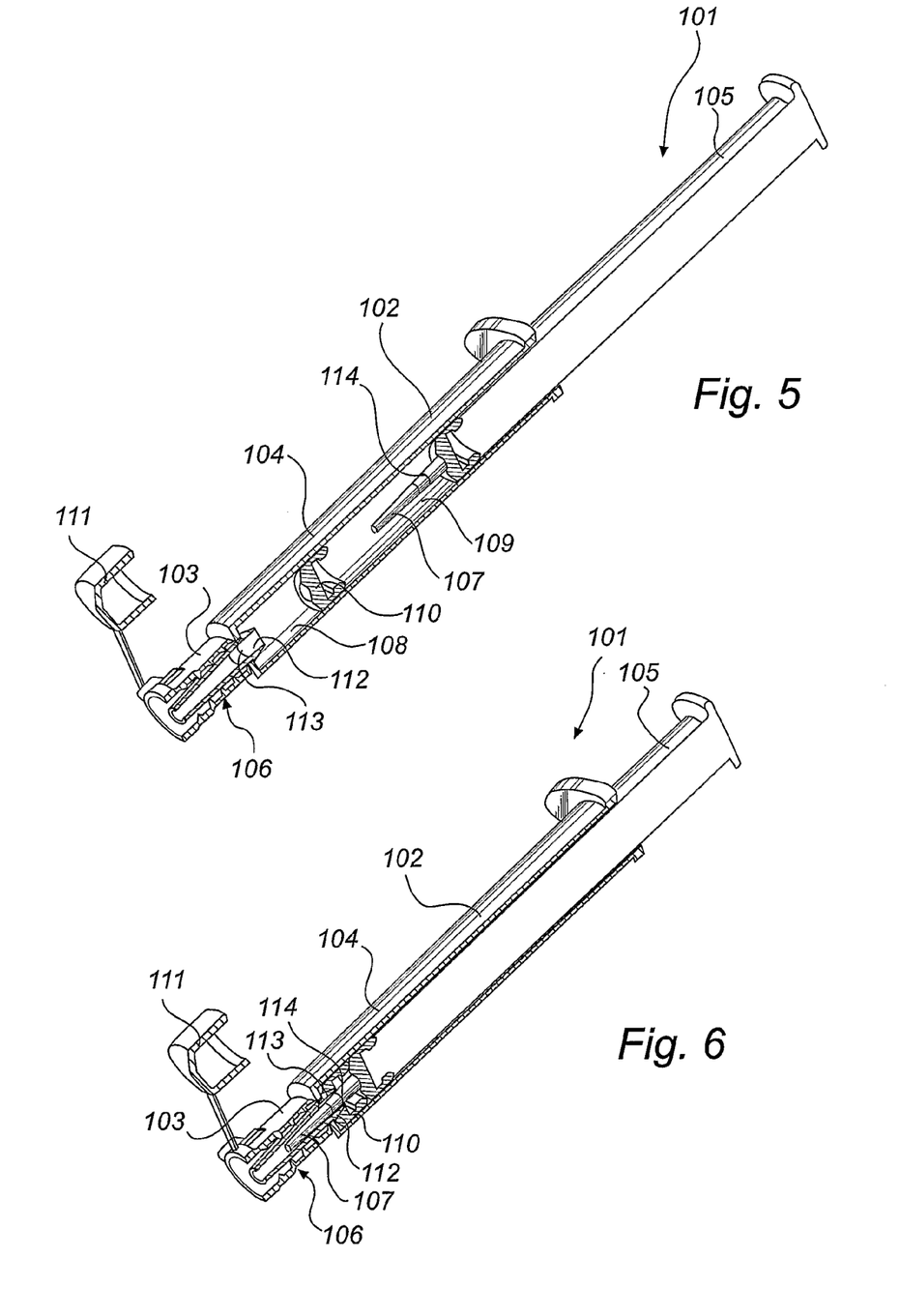
FIG. 5 is a cross-sectional view of the applicator device of FIG. 4 shown before the plunger is pressed.
FIG. 6 is a view corresponding to FIG. 5, but shown when the plunger has been pressed all the way down.

In the embodiment of FIGS. 4-6, the applicator device 101 is similar to the applicator device 1 of FIG. 1, except that the applicator device 101 has a housing 104 which is divided into two compartments 108, 109 delimited by a divider in the form of a frangible membrane 110. With the plunger 105 the membrane 110 forms an expulsion arrangement for expelling solution form the syringe. The tip end compartment 108 is filled with flushing solution, e.g. saline solution, and the back end compartment 109 is filled with a lock solution. A frangible tip 107 is attached to the plunger 105. The tip end 106 of the housing 104 is provided with a mandrel 112 arranged in a semicircle. The mandrel 112 has a sharp forward cutting edge for rupturing the membrane 110.

As with the applicator device 1 of FIG. 1, the applicator device 101 is connected to a catheter or other access system via the connector 103. As the plunger 105 is pressed, first the saline solution of the first compartment 108 is injected into the catheter. When all saline solution has been injected, the membrane 110 has reached the tip end 106 of the housing 104. The membrane 110 is then ruptured by the mandrel 112 and continued pressing of the plunger 105 injects the lock solution of the second compartment 109. As the plunger 105 is pressed all the way down, the tip 107 engages the inside of the connector 103 in the same way as in the first embodiment, as can be seen in FIG. 6. Therefore, as the syringe 102 is removed, the tip 107 and the tip end 106 of the housing 104 are left behind, closing the opening of the catheter. As with the first embodiment, this embodiment ensures that sterility is maintained in the catheter. Furthermore, the applicator device 101 of this second embodiment simplifies the rinsing and locking of the catheter since it obviates the need for a separate syringe for the flushing solution. When the syringe 102 has been removed, a lid 111 is placed over the connector 103.

Figure 7:
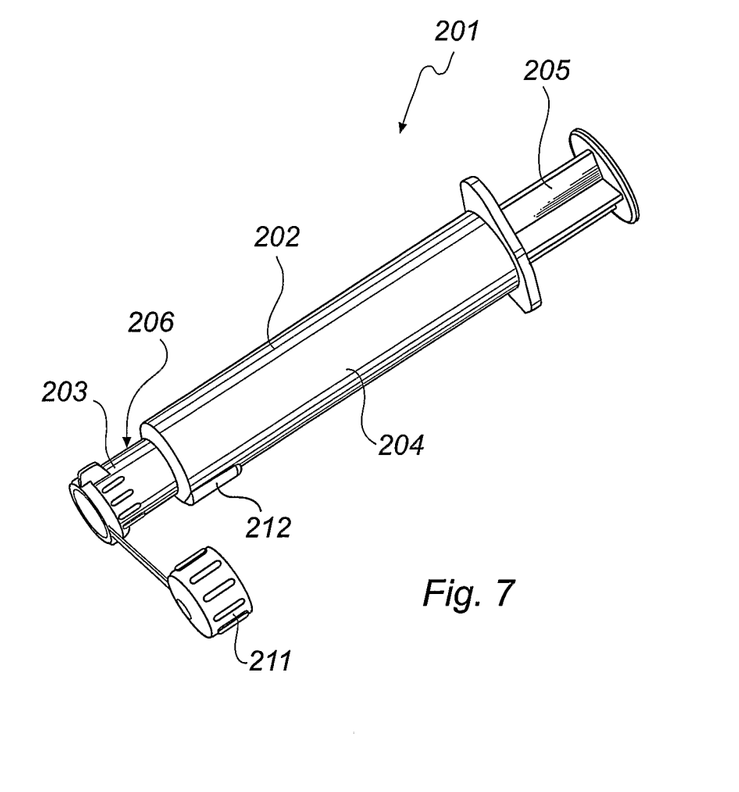
FIG. 7 is a perspective view of an applicator device according to a third embodiment of the invention with two compartments and a by-pass.
Figure 8:
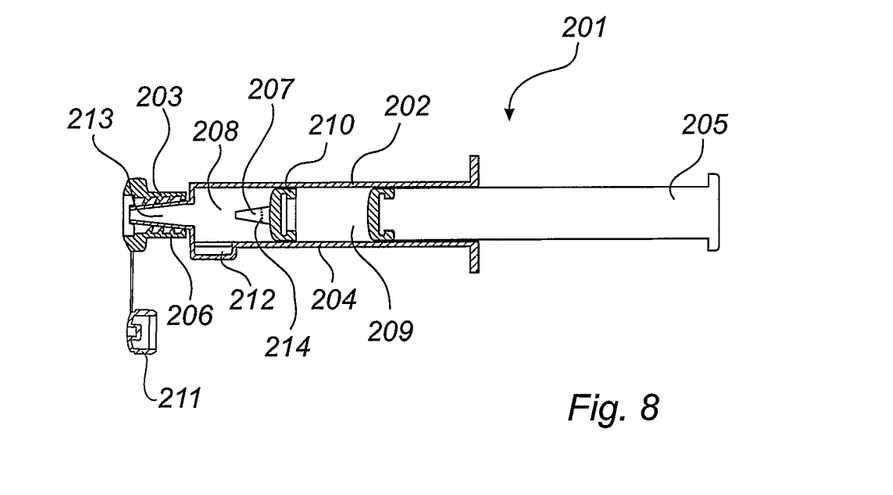
FIG. 8 is a cross-sectional view of the applicator device of FIG. 7 shown before the plunger is pressed.
Figure 9:
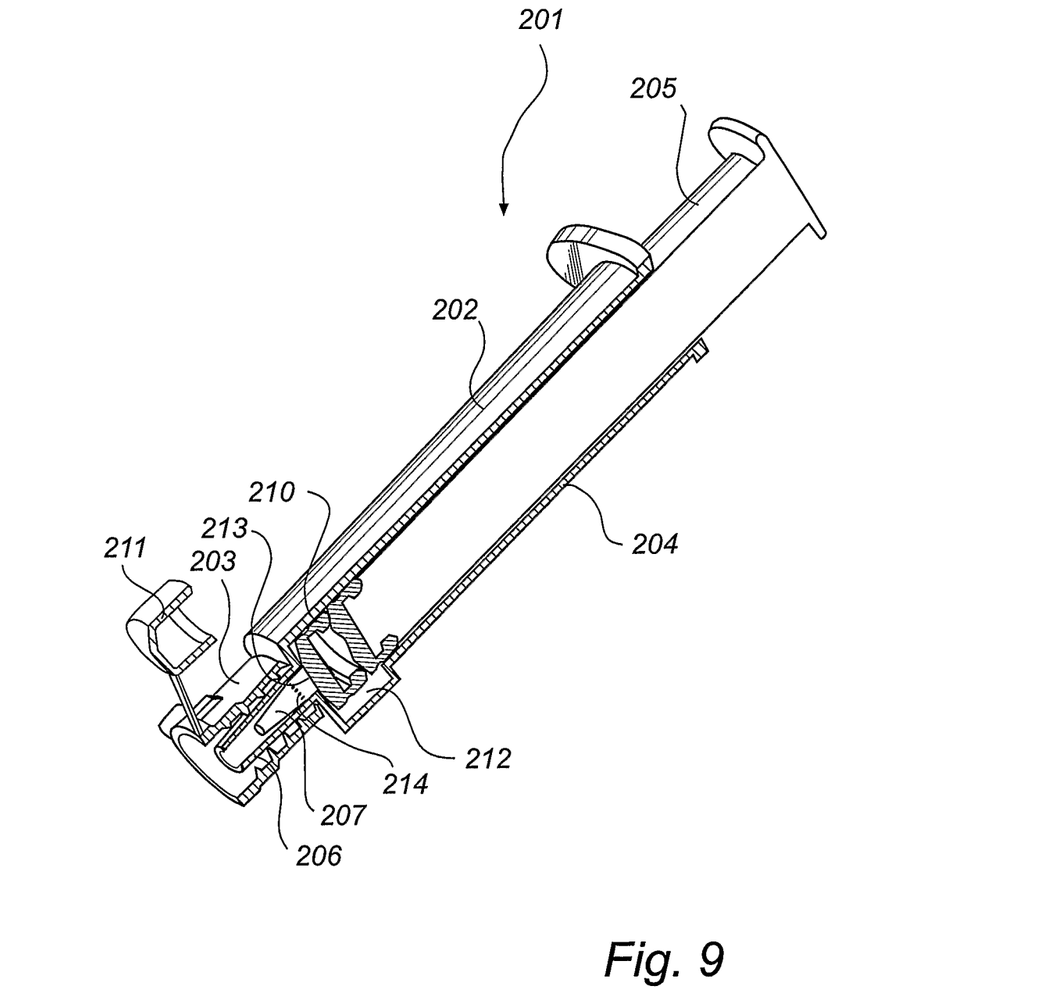
FIG. 9 is a view corresponding to FIG. 8, but shown when the plunger has been pressed all the way down.

In the embodiment of FIGS. 7-9 the applicator device 201 is similar to the applicator, device 101 of FIG. 4, but is provided with a by-pass 212 near the tip end 206 of the housing 204, and not provided with a mandrel. Just as in the device 101, the plunger 205 and a divider, in this case in the form of a non-frangible membrane 210, form an expulsion arrangement for expelling solution from the syringe 202. In contrast to the device 101, the frangible tip 207 is arranged on the membrane 210 and not on the plunger 205.

As with the applicator devices of FIGS. 1 and 4, the applicator device 201 is connected to a catheter via the connector 203. As the plunger 205 is pressed, first the flushing solution (e.g. saline solution) of the first compartment 208 is injected into the catheter. When all saline solution has been injected, the membrane 210 has reached the tip end 206 of the housing 204. Continued pressing of the plunger 205 injects the lock solution of the second compartment 209. Since the membrane 210 blocks the outlet passage 213 at the tip end 206 of the housing 204, the lock solution by-passes the membrane 210 via the by-pass 212. As the plunger 205 is pressed all the way down, the tip 207 which is attached to the membrane 210 is pushed all the way down and engages the inside of the connector 203 in the same way as in the first and second embodiments, as can be seen in FIG. 9. Therefore, as the syringe 202 is removed, the tip 207 is left behind. The tip end 206 of the housing 204 is also broken off and left behind. Just as with the first and second embodiments, this embodiment ensures that sterility is maintained in the catheter. Furthermore, the applicator device 202 of this third embodiment simplifies the rinsing and locking of the catheter since it obviates the need for a separate syringe for the flushing solution. When the syringe 202 has been removed, a lid 211 is placed over the connector 203.

In the embodiment of FIGS. 10-13, the applicator device 301 is similar to the applicator devices of FIGS. 4 and 7, except that the two compartments 308, 309 are delimited by a seal 311. With the plunger 305, the seal 311 forms an expulsion arrangement for expelling solution from the syringe 302. As in the second and third embodiments, the tip end compartment 308 is filled with flushing solution (e.g. saline solution) and the back end compartment 309 is filled with a lock solution. The seal 311 that separates the two compartments 308, 309 is provided with a frangible tip 307 corresponding to the tip 7 in the first embodiment.

Figure 12:
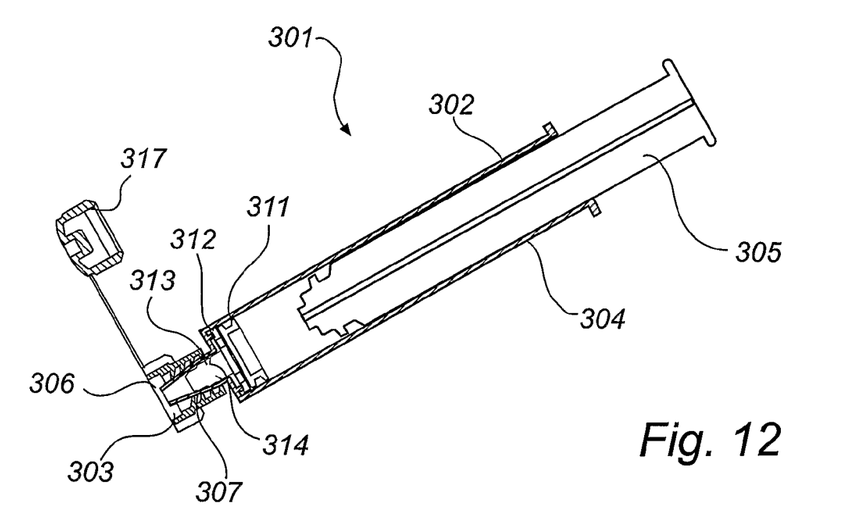
FIG. 12 is a view corresponding to FIG. 11, but shown when the plunger has been pressed part of the way down and the first compartment has been emptied.
Figure 13:
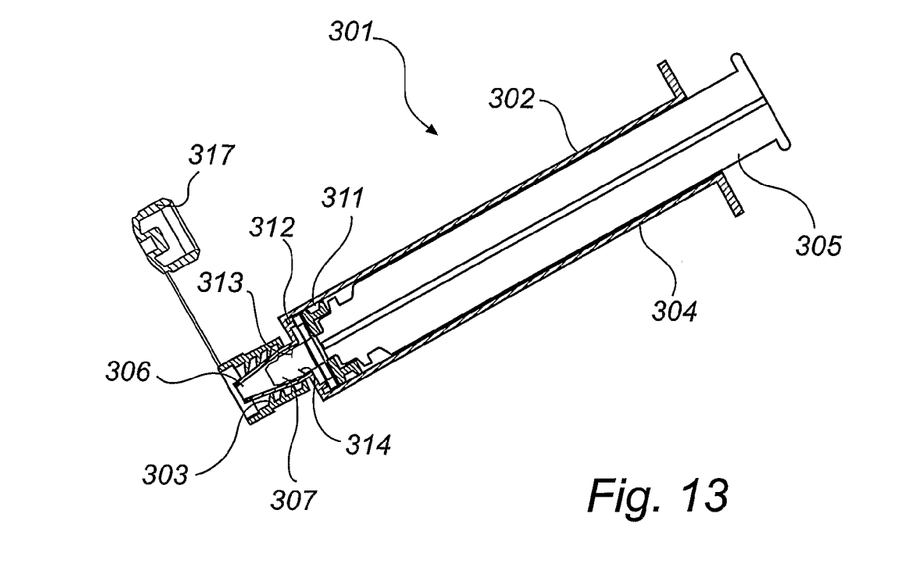
FIG. 13 is a view corresponding to FIG. 12, but shown when the plunger has been pressed all the way down.
Figure 14:
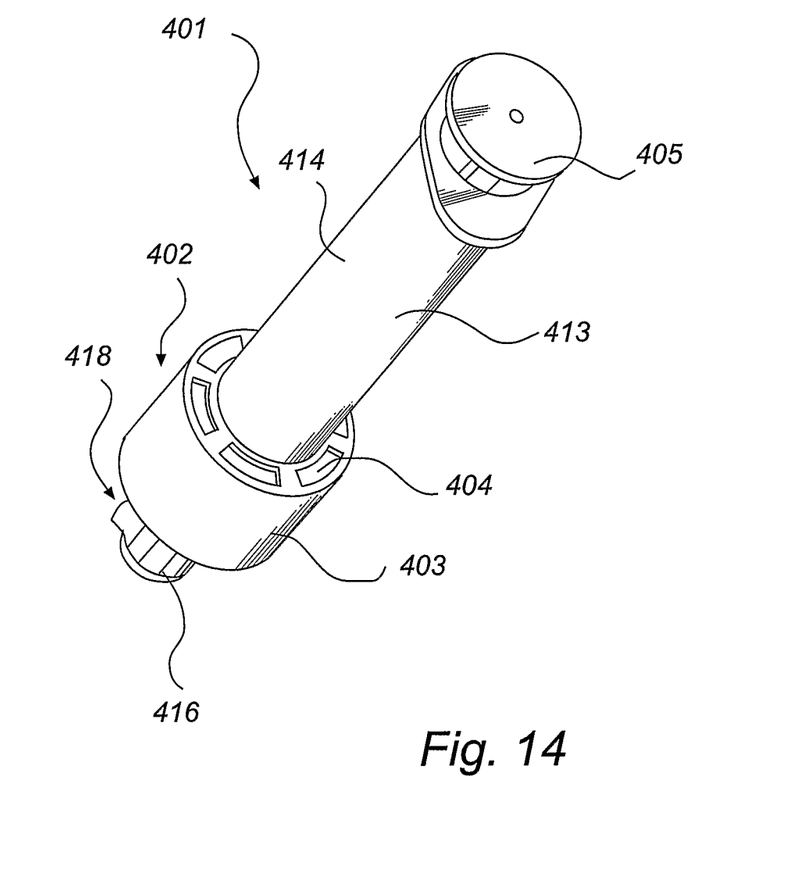
FIG. 14 is a perspective view of an applicator device according to a fifth embodiment of, the invention with an air removal system.
Figure 15:
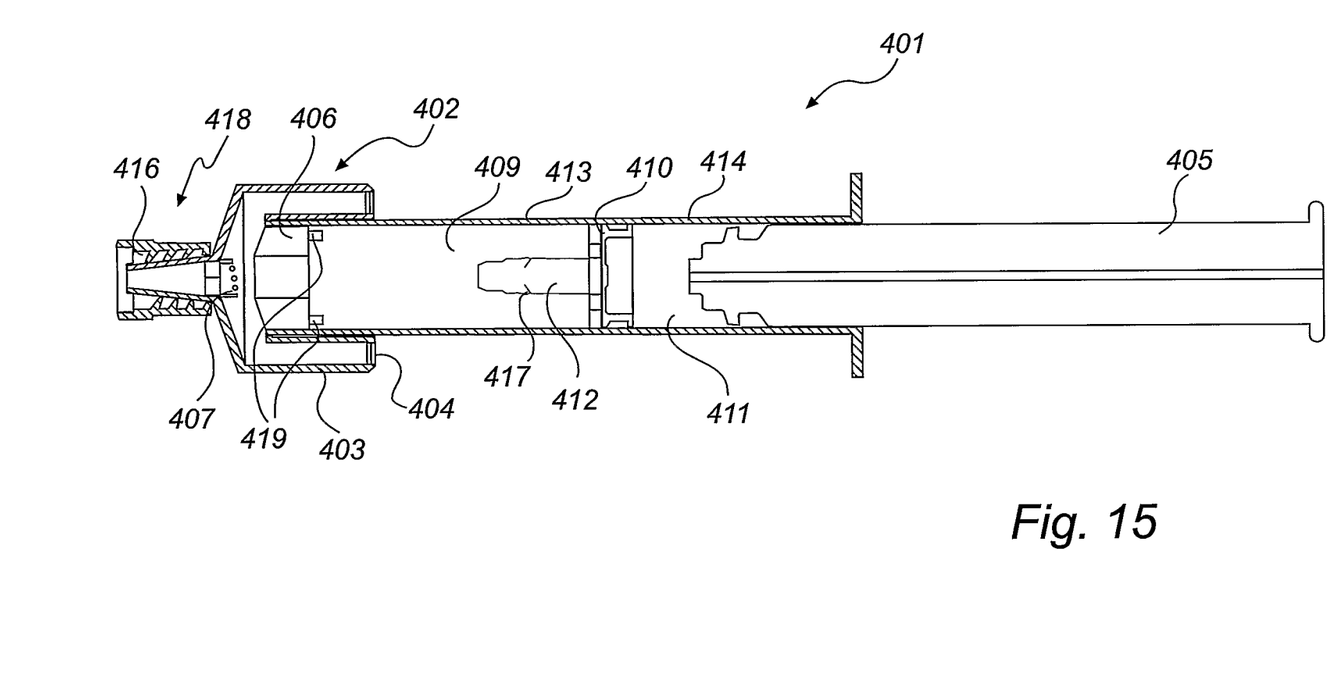
FIG. 15 is a cross-sectional view of the applicator device of FIG. 14 shown before the plunger is pressed.

As with the applicator devices of the other embodiments, the applicator device 301 is connected to a catheter or other access system via the connector 303. As the plunger 305 is pressed, first the flushing solution of the first compartment 308 is injected into the catheter. When all flushing solution has been injected, the seal 311 has reached the tip end 306 of the housing 304, as can be seen in FIG. 12. Through continued pressing of the plunger 305 a valve in the seal is opened and the lock solution of the second compartment 309 can be injected. The valve in the seal 311 is constituted by slits in the seal 311, which are normally closed, but which open when the seal impacts spacers 312 at the tip end 306 of the housing 304. As the plunger 305 is pressed all the way down, the tip 307 is also pressed all the way down and engages the inside of the connector 303 in the same way as in the other embodiments, as can be seen in FIG. 13. Therefore, as the syringe 302 is removed, the tip 307 is left behind, closing the opening of the catheter. The tip end 306 of the housing 304 is also broken off and left in the connector 303. As with the three other embodiments, this embodiment ensures that sterility is maintained in the catheter. Furthermore, the applicator device 302 of this fourth embodiment simplifies the rinsing and locking of the catheter since it obviates the need for a separate syringe for the flushing solution. When the syringe 302 has been removed, a lid 317 is placed over the opening of the connector 303.

Figure 10:
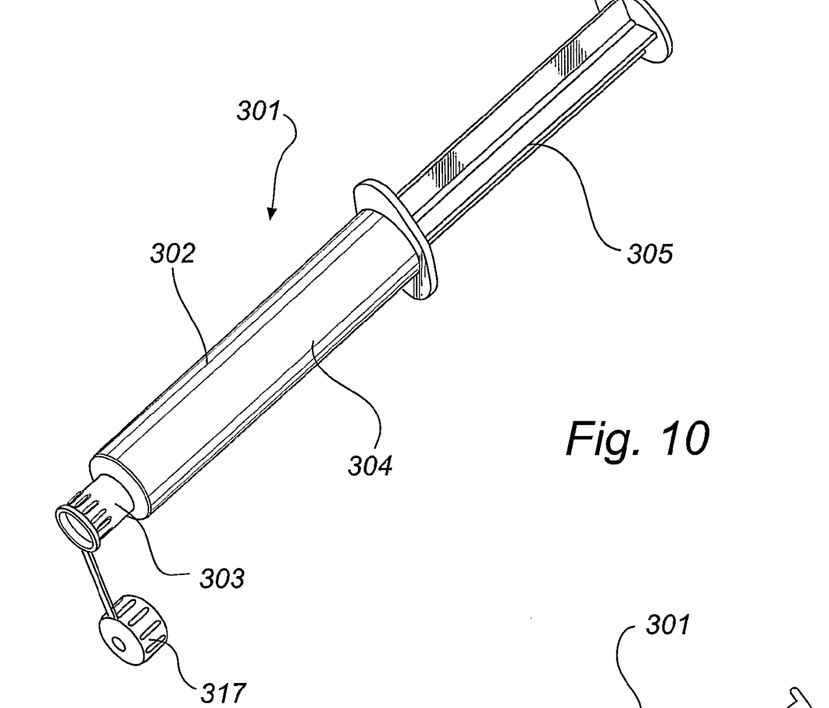
FIG. 10 is a perspective view of an applicator device according to a fourth embodiment of the invention with two compartments and a valve function.
Figure 11:
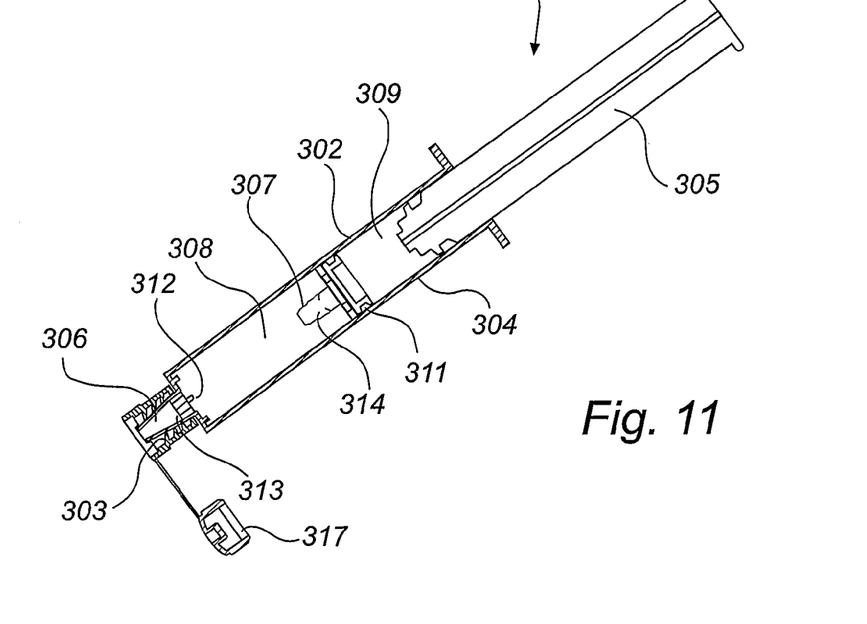
FIG. 11 is a cross-sectional view of the applicator device of FIG. 10 shown before the plunger is pressed.

In the embodiment of FIGS. 14-17, the applicator device 401 is similar to the applicator device of FIGS. 10-12, except that this fifth embodiment includes an air removal system 402, which consists of a separate chamber 403 of the applicator 401 with an air permeable membrane 404, such that the pressure in the chamber 403 is similar to the atmospheric pressure $p_2$ outside the applicator 401. When the catheter is connected with the applicator 401, the air removal system 402 communicates with the catheter. The blood pressure $p_1$ in the catheter is higher than the pressure $p_2$ in the chamber 403. The blood with air bubbles will therefore flow into the chamber 403. When the chamber is filled with blood, the plunger 405 is pressed down, so that the stopper 406 moves downwards and becomes penetrated by the mandrel 407. When the stopper 406 is pressed all the way down, the blood with air is enclosed in the chamber 403. By pressing the plunger 405 further down, the rinsing solution in the forward compartment 409 is pressed into the catheter. With the plunger 405, the seal 410 forms an expulsion arrangement for expelling solution from the applicator 401. The back end compartment 411 is filled with a lock solution. The valve 410 that separates the tip end compartment 409 with the rinsing solution from the back end compartment 411 is provided with a frangible tip 412.

Figure 16:
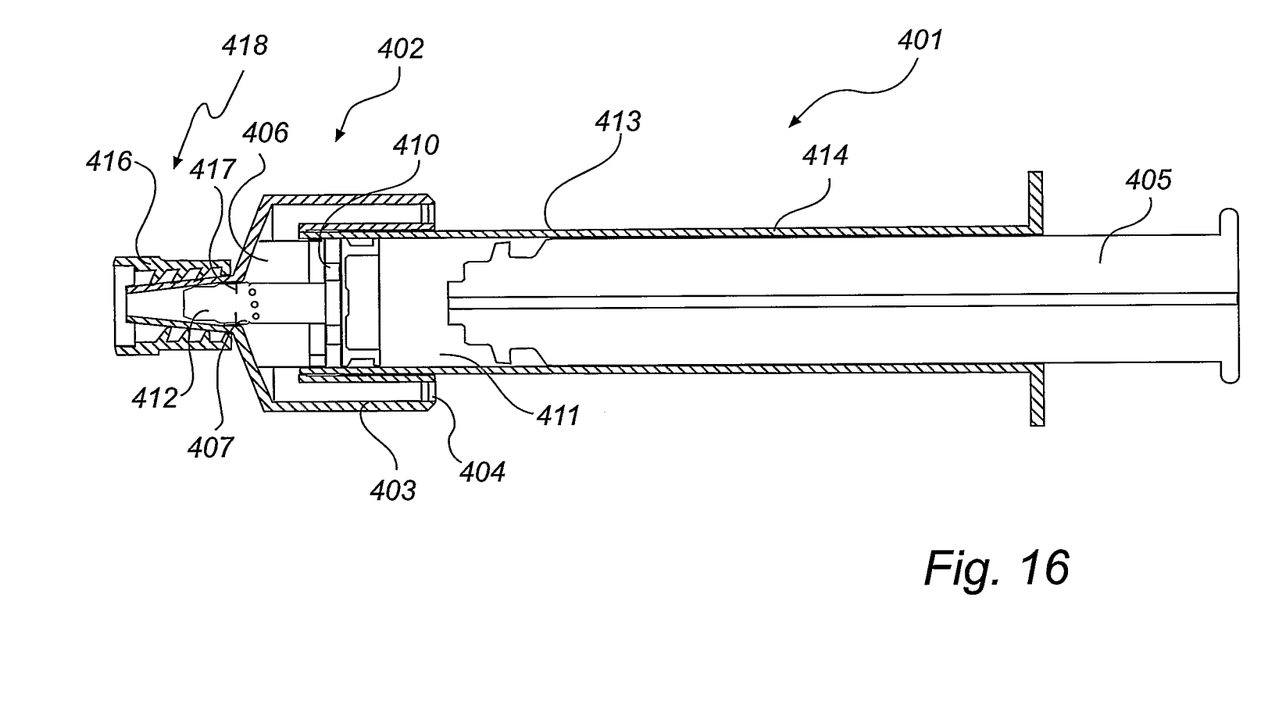
FIG. 16 is a view corresponding to FIG. 15, but shown when the plunger has been pressed part of the way down and the first compartment has been emptied.
Figure 17:
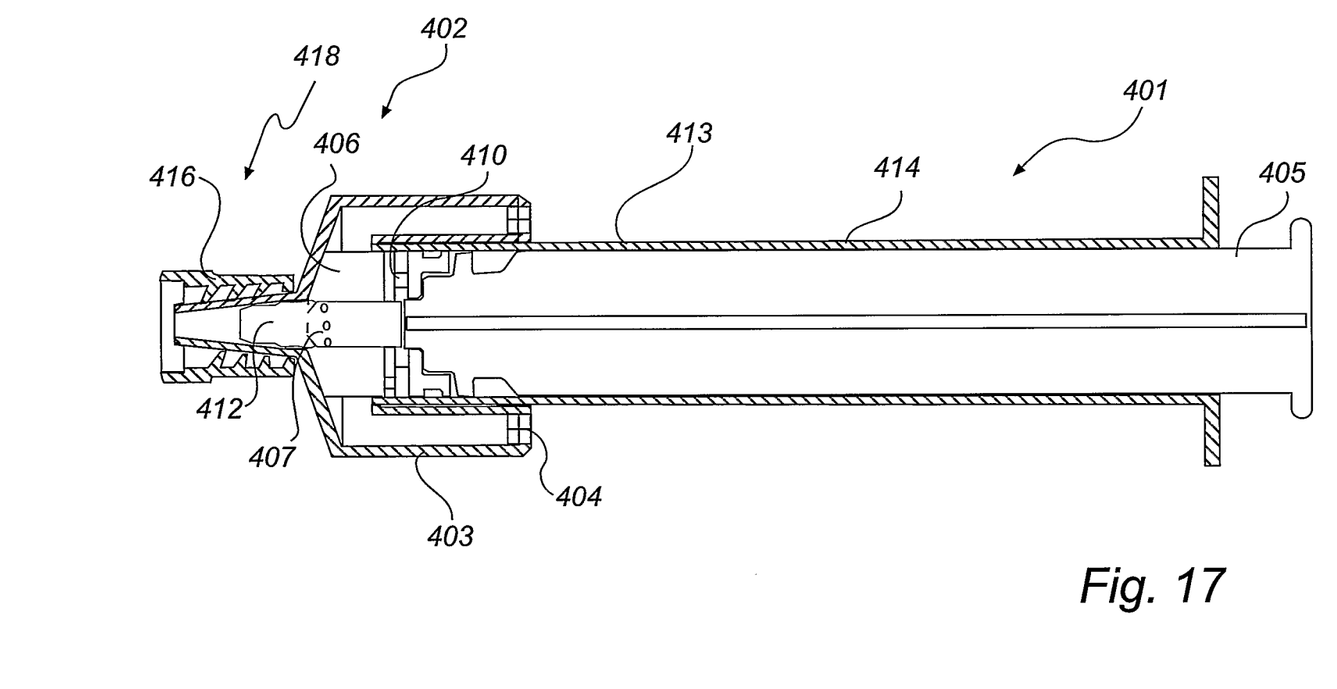
FIG. 17 is a view corresponding to FIG. 16, but shown when the plunger has been pressed all the way down.

When all rinsing solution has been injected into the catheter, the valve 410 has reached the tip end of the housing, as can be seen in FIG. 16. By continued pressing of the plunger 405, a valve 410 in the seal is opened and the lock solution of the back end compartment 411 can be injected into the catheter. The valve 410 in the seal is constituted by slits in the seal, which are normally closed, but which open when the seal impacts spacers 419 at the tip end of the housing. As the plunger 405 is pressed all the way down, the tip 412 is also pressed all the way down and engages the inside of the tip end of the housing and the luer lock in the same way as in the other embodiments described above. Therefore, as the syringe 413 is removed, the tip 412 is left behind, closing the opening of the catheter. The tip end of the housing is also broken off and left in the luer lock.

The skilled person realises that a number of modifications of the embodiments described herein are possible without departing from the scope of the invention, which is defined in the appended claims.

For instance, the two-compartment applicator device 101; 201; 301 may be provided with a small abutment on the plunger 105; 205; 305, so that the nurse or physician is given an indication when the tip end compartment 108; 208; 308 has been emptied. The plunger 105; 205; 305 may then be pressed further, past the abutment, for emptying the back end compartment. Otherwise, the injection of the flushing solution and the lock solution may be done in one continuous push.

The two-compartment applicator device 101; 201; 301 or an applicator with more than two compartments, may also be suitable in cases where the components of the lock solution need to be stored separately during sterilization and storage. In such cases, distilled water or a simple buffer solution is contained in one compartment and other components in dry form or in high concentrations are contained in the other compartment(s).

The invention claimed is:

1. A device for applying a lock solution in a catheter or access system comprising:
    a syringe having an expulsion arrangement for expelling the lock solution from the device, said expulsion arrangement including a plunger arranged in a housing of a portion of the syringe;
    a sterile connector for connecting the syringe to the catheter, the sterile connector being configured to engage a tip end of the syringe when the tip end of the syringe is inserted in the connector, wherein a tip of the expulsion arrangement is configured to be advanced into the connector, wherein the connector is arranged to prevent the tip of the expulsion arrangement from entering the catheter, wherein the tip of the expulsion arrangement is frangible and configured to break off from the expulsion arrangement, and the tip end of the syringe is configured to break off from the syringe, when the syringe is removed from the connector; and
    a lid coupled to the connector and configured to cover an end of the connector disconnected from the syringe.

2. A device according to claim 1, wherein said sterile connector is a luer lock.

3. A device according to claim 1, wherein the frangible tip of the expulsion arrangement comprises a peripheral row of indentations.

4. A device according to claim 1, wherein the frangible tip of the expulsion arrangement comprises a substantially radial projection and the sterile connector comprises an inside.

5. A device according to claim 1, wherein the tip of the expulsion arrangement comprises a conical shape.

6. A device according to claim 1, wherein the housing comprises a first and a second compartment.

7. A device according to claim 6, wherein the first compartment being configured in a front end of the housing, is filled with flushing solution and the second compartment being configured in a back end of the housing, is filled with a lock solution.

8. A device according to claim 7, wherein the plunger comprises an abutment means for indicating when the flushing solution has been emptied from the first compartment.

9. A device according to claim 6, wherein the expulsion arrangement further comprises a divider separating the first and second compartments.

10. A device according to claim 9, wherein the divider comprises a frangible membrane, and wherein a mandrel configured at the tip end of the syringe is configured to rupture the frangible membrane.

11. A device according to claim 9, wherein the tip of the expulsion arrangement is configured on the divider.

12. A device according to claim 11, further comprising a by-pass configured to shunt the lock solution past the divider.

13. A device according to claim 9, wherein the divider comprises a seal including a valve operable by compressing the plunger.

14. A device according to claim 6, further comprising an air removal system.

15. A device according to claim 14, wherein the air removal system comprises a chamber separated from the atmosphere by an air permeable membrane, said chamber being configured to communicate with said catheter or access system when said syringe is connected to said catheter or access system.

16. A device according to claim 1, wherein the tip of the expulsion arrangement is configured on the plunger.

17. A method of applying a lock solution in a catheter or access system, comprising the steps of:
    connecting a sterile connector attached to a tip end of a syringe to the catheter or other access system;
    injecting the lock solution in the catheter by compressing an expulsion arrangement of the syringe including a plunger, thereby advancing a frangible tip of the expulsion arrangement into the sterile connector;
    removing the syringe from the sterile connector, leaving behind the frangible tip of the expulsion arrangement and the tip end of the syringe, wherein the frangible tip of the expulsion arrangement is broken off during the step of removing the syringe; and
    closing a lid on the sterile connector.

18. A method according to claim 17, further comprising the step of injecting a flushing solution in the catheter for rinsing the catheter prior to the step of injecting the lock solution.

19. A method according to claim 18, wherein the flushing solution is injected by a first compression of the plunger and the lock solution is injected by a second compression of the plunger.

20. A method according to claim 18, wherein the flushing solution and subsequently the lock solution are injected during one continuous compression of the plunger.

* * * * *